United States Patent
Li et al.

(10) Patent No.: US 10,485,633 B2
(45) Date of Patent: Nov. 26, 2019

(54) MOLDED DENTAL ROOT CANAL FILLING POINTS/CONES AND PROCESS OF MAKING SAME

(71) Applicant: TULSA DENTAL PRODUCTS LLC, Tulsa, OK (US)

(72) Inventors: Nathan Y. Li, Malibu, CA (US); DaQing Wu, Beijing (CN)

( * ) Notice: Subject to any disclaimer, the term of this patent is extended or adjusted under 35 U.S.C. 154(b) by 742 days.

(21) Appl. No.: 14/181,621

(22) Filed: Feb. 14, 2014

(65) Prior Publication Data

US 2014/0315155 A1 Oct. 23, 2014

Related U.S. Application Data

(60) Provisional application No. 61/764,935, filed on Feb. 14, 2013, provisional application No. 61/764,927, filed on Feb. 14, 2013.

(51) Int. Cl.
*A61C 5/50* (2017.01)
*A61C 13/20* (2006.01)

(52) U.S. Cl.
CPC .............. *A61C 5/50* (2017.02); *A61C 13/206* (2013.01); *A61C 13/20* (2013.01)

(58) Field of Classification Search
CPC ..... A61C 5/04; A61C 13/206; A61C 13/0006; A61C 13/20; B29C 2045/2777; B29C 45/2737
See application file for complete search history.

(56) References Cited

U.S. PATENT DOCUMENTS

| | | | | |
|---|---|---|---|---|
| 4,140,470 A | * | 2/1979 | Pasch ..................... | B29C 45/02 425/544 |
| 4,362,508 A | * | 12/1982 | Soderstrom .............. | A61C 5/04 433/220 |
| 4,525,147 A | * | 6/1985 | Pitz ........................ | A61C 5/04 433/224 |
| 5,190,702 A | * | 3/1993 | Johnson .................. | A61C 5/50 264/102 |
| 5,302,129 A | | 4/1994 | Heath et al. | |

(Continued)

FOREIGN PATENT DOCUMENTS

EP 2298226 3/2011

OTHER PUBLICATIONS

Wikepedia—Injection Molding Machine (https://en.wikipedia.org/wiki/Injection_molding_machine).*

(Continued)

*Primary Examiner* — Anthony Calandra
*Assistant Examiner* — Jerzi H Moreno Hernandez
(74) *Attorney, Agent, or Firm* — Dentsply Sirona Inc.

(57) ABSTRACT

The present invention provides an improved root canal filling point/cone that can be manufactured precisely to result in better obturation with less micro-leakage. One aspect of the present invention is directed to a molded root canal filling point/cone. Another aspect of the present invention is directed to a thermo-pressure molding process for manufacturing root canal filing appliances (e.g., Gutta Percha points). Another aspect of the present invention is directed to the structure of the mold for undertaking thermo-injection molding. A further aspect of the present invention is directed to a production line comprising the thermo-injection process.

18 Claims, 13 Drawing Sheets

(56) References Cited

U.S. PATENT DOCUMENTS

| | | | | |
|---|---|---|---|---|
| 5,525,050 | A * | 6/1996 | Takizawa | B29C 45/78 264/40.6 |
| 5,540,766 | A * | 7/1996 | Castellani | A61K 6/0038 106/35 |
| 5,686,122 | A * | 11/1997 | Huntington | B29C 33/0083 425/547 |
| 6,024,569 | A * | 2/2000 | Ohne | A61C 5/50 433/224 |
| 6,227,210 | B1 * | 5/2001 | Wyss | A61C 15/041 132/323 |
| 6,767,209 | B1 * | 7/2004 | Tomita | A46B 1/00 132/329 |
| 6,938,669 | B2 * | 9/2005 | Suzuki | B22D 17/007 164/113 |
| 7,252,508 | B2 * | 8/2007 | Karmaker | A61C 5/04 433/224 |
| 2003/0113686 | A1 * | 6/2003 | Jia | A61K 6/0023 433/81 |
| 2004/0137403 | A1 * | 7/2004 | Koch | A61C 5/04 433/81 |
| 2005/0003328 | A1 * | 1/2005 | Karmaker | A61C 13/30 433/220 |
| 2005/0226956 | A1 * | 10/2005 | Fischer | B29C 45/27 425/549 |
| 2006/0197254 | A1 * | 9/2006 | Onishi | B29C 48/53 264/211.21 |
| 2006/0204934 | A1 | 9/2006 | Mannschedel et al. | |
| 2008/0199832 | A1 * | 8/2008 | Mannschedel | A61C 5/04 433/224 |
| 2008/0241300 | A1 * | 10/2008 | Kasahara | B29C 45/1781 425/144 |
| 2008/0274439 | A1 * | 11/2008 | Gutzner | A61C 5/04 433/102 |
| 2009/0230756 | A1 | 9/2009 | Crossman | |
| 2011/0129793 | A1 | 6/2011 | Goodis | |
| 2011/0256255 | A1 * | 10/2011 | Guo | B29C 45/34 425/420 |
| 2012/0040045 | A1 * | 2/2012 | Ciccone | B29C 33/303 425/577 |
| 2012/0135377 | A1 * | 5/2012 | Klee | A61C 5/02 433/141 |
| 2012/0315351 | A1 * | 12/2012 | Oh | B29C 45/73 425/552 |
| 2013/0056908 | A1 | 3/2013 | Goodis et al. | |
| 2013/0334727 | A1 * | 12/2013 | Mine | B29C 45/0003 264/139 |

OTHER PUBLICATIONS

International Search Report of Counterpart PCT International Application No. PCT/US2014/016631.

International Search Report of Counterpart PCT International Application No. PCT/US2014/017852.

* cited by examiner

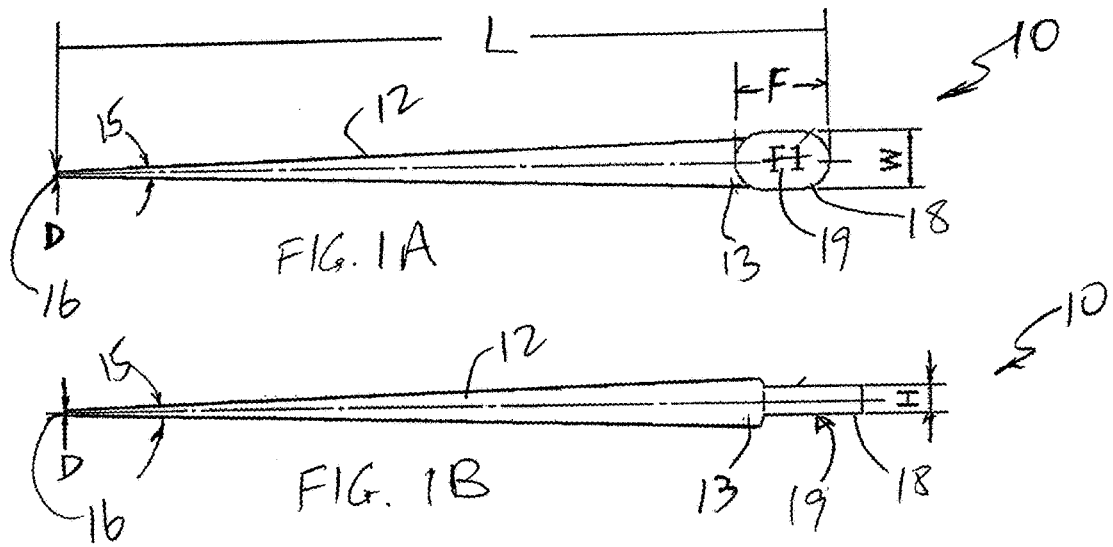
FIG. 1A
FIG. 1B
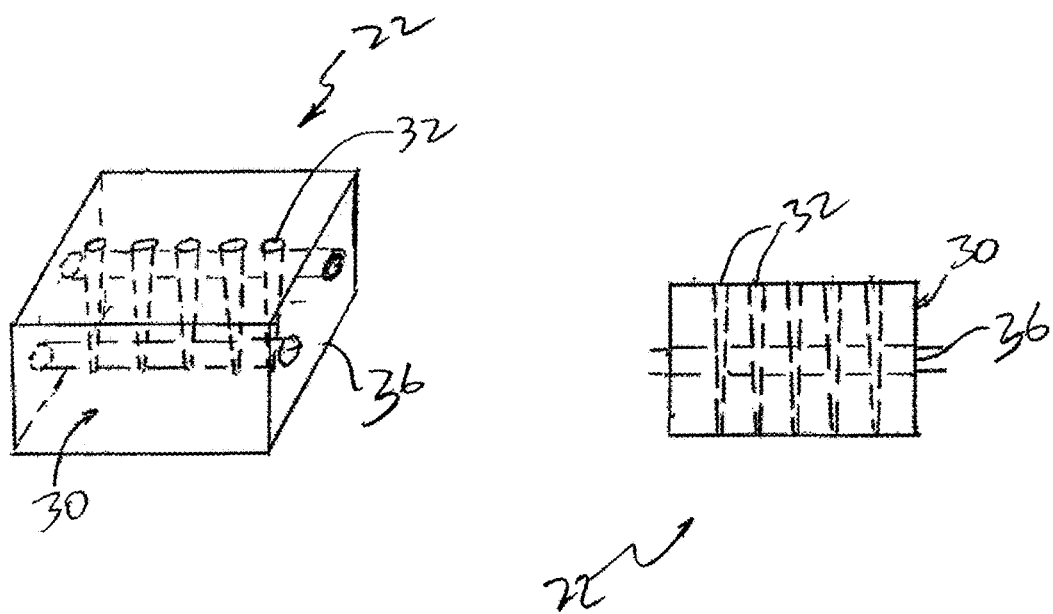
FIG. 2A
FIG. 2B

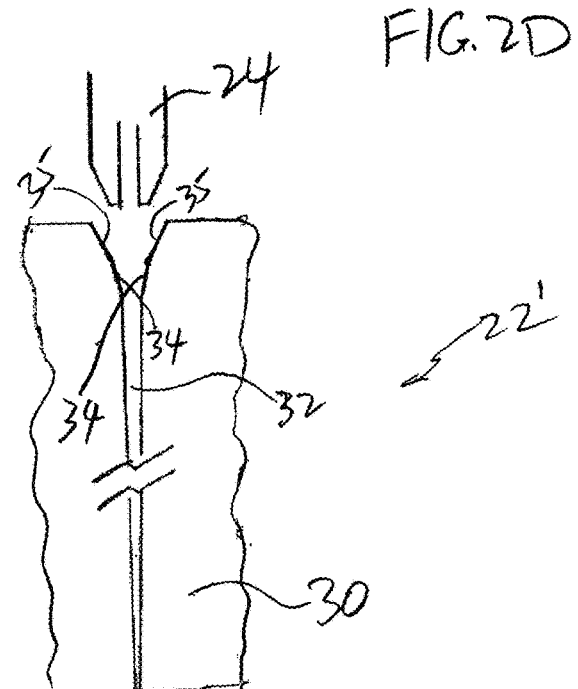
FIG. 2D
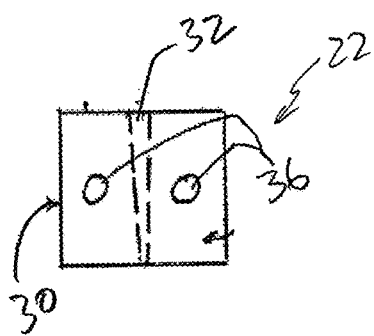
FIG. 2C
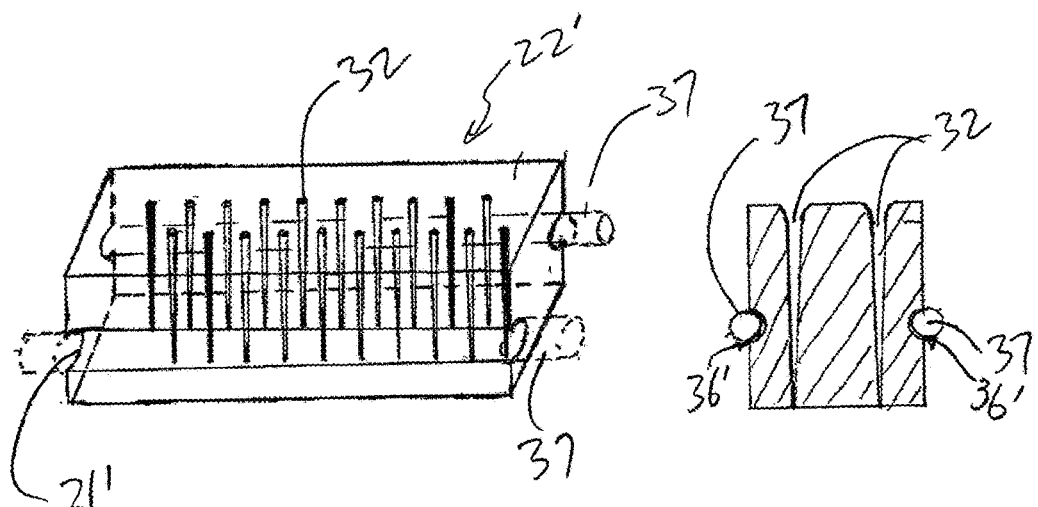
FIG. 3A
FIG. 3B

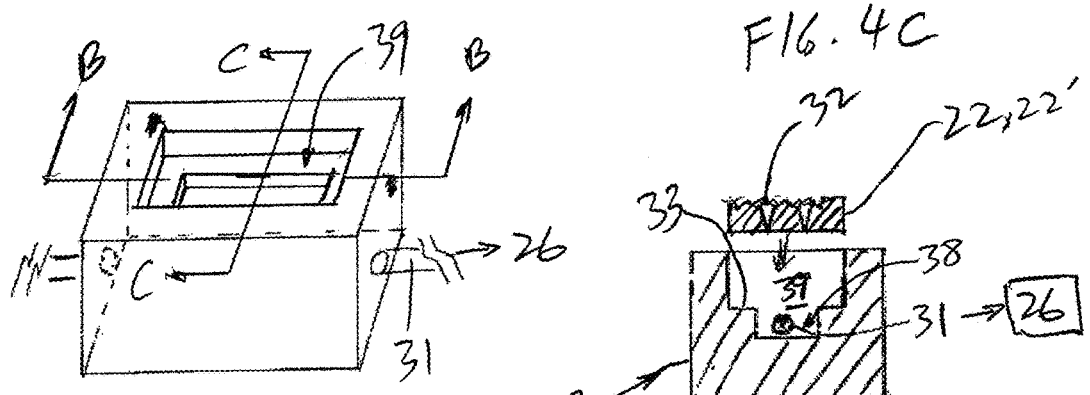
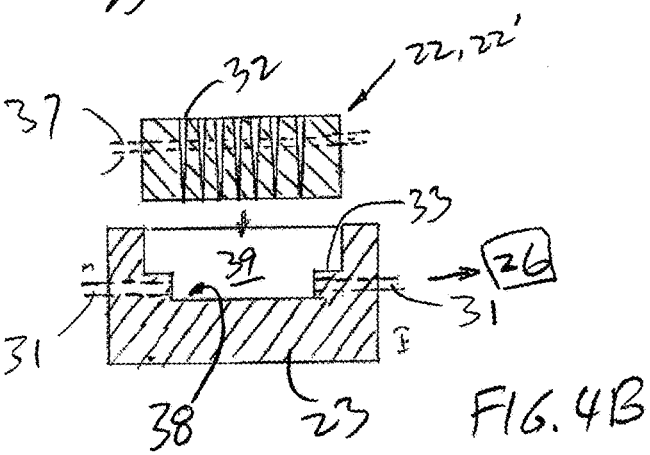
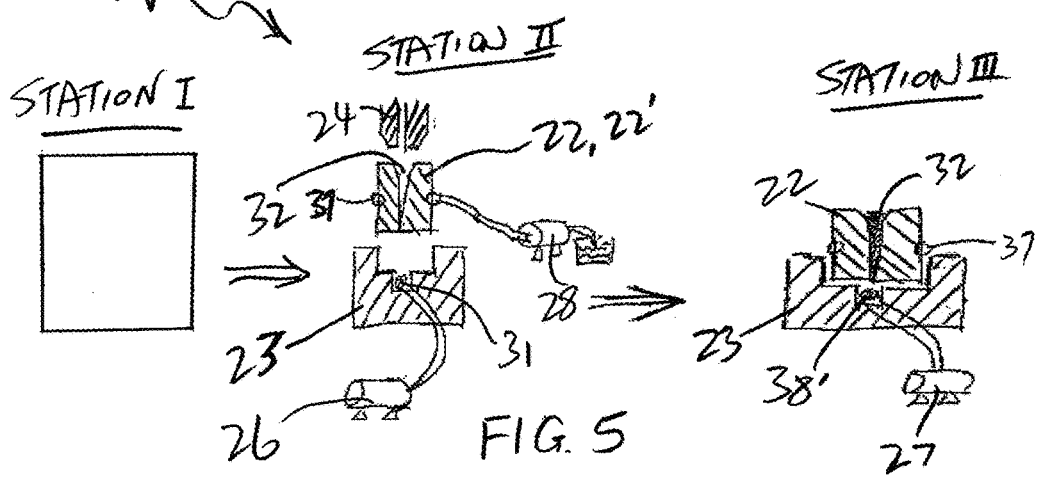

MOLDED DENTAL ROOT CANAL FILLING POINTS/CONES AND PROCESS OF MAKING SAME

BACKGROUND OF THE INVENTION

1. Field of the Invention

The present invention is directed to materials for filling dental root canals.

2. Description of Related Art

Dental root canal treatment generally involves three stages: shaping, cleaning and obturation (generally involving filling and sealing). The purpose of performing dental root canal treatment is to remove infected dental pulp tissue inside the pulp chamber and root canals, and to fill/seal the vacant space with a biocompatible material. More specifically, the ultimate objective of root canal treatment is to eliminate the infection inside the dental root system and to tightly seal or obturate, in three dimensions (3-D), the tiny openings at the end of the root canal, (referred in the profession as an apex). Failure to completely seal the apex or the root canal in 3-D leads to micro-leakage, which will lead to future bacteria colonization inside the root canal system, and re-infection and possible loss of the tooth. Micro-leakage is the most common cause of tooth failure.

Heretofore, root canal treatment processes involve placement of a root canal filling or sealing point or cone in a prepared root canal to plug the root canal, ideally in a manner to eliminate micro-leakage. In the past twenty-plus years, leading dentists and scientists have improved and revolutionized the shaping and cleaning part of the root canal treatment process. But the basic filling technique still lags behind due to antiquated manufacturing process dated more than 50 years ago. The existing filling points and the process of application thereof do not lend themselves well to providing a good seal of the root canal apex.

The most commonly used root canal filling material for many years is a biocompatible latex compound commonly called Gutta Percha, which comprises trans-polyisoprene, with a chemical composition of 1,4-trans-polyisoprene (TPI). Gutta Percha can be softened by heat to increase its plasticity comparing to other rubber based material. It is chemically inert therefore it is more biocompatible. Gutta Percha also hold its dimension quite well when change from heated liquid alpha phase to cooled solid beta stage.

The way to use Gutta Percha to fill/seal the root canal is to make it into a tapered cone shape "cone" or "point", commonly called Gutta Percha point or cone (hereinafter throughout the present disclosure, "point" and "cone" are used interchangeably to refer to the root canal filling material). Heretofore, root canal filling points are formed of a filling material that is shaped into slender cones each having a small taper angle (e.g., 5-10 degrees). Each point is made into a particular taper shape that matches the shaping instrument (file) used by dentists to shape a root canal cavity for subsequent filling. The traditional way of making these points is by manual labor, specifically hand rolling Gutta Percha material into points to match shaping files. The Gutta Percha material needs to be softened first with higher temperature. Then being rolled into the point while being cooled to hold the final shape. This method of making the points has been in existence for over 50 years without much change. It is grossly inaccurate and risks material contamination since it is mostly handled by human hands.

There are a few automated and/or semi-automatic systems designed to make Gutta Percha points. They share same basic design approach, which mimic human hands rolling motion. These machines either use two rollers or one roller against one moving belt to roll points. There are several short comings with these machines. They are rather unstable and not efficient enough. They need constant adjustments for accuracy. Further, they are limited to rolling cones using only Gutta Percha based materials but not materials that have a different consistency compared to Gutta Percha materials.

U.S. Pat. No. 5,089,183 discloses a method of manufacturing appliances for use in filling endodontically prepared root canals with filler material, which involves inserting a shaft of a carrier into an uncured Gutta Percha material provided in a cavity of a block, heating and allowing the material to adhere to the carrier shaft. This process is low throughput, as it adds further complication to the making of a filler point for root canal.

It can be seen that the current root canal treatment procedures involve complex and challenging steps, which use cones that may be improperly shaped, which result in poor obturation leading to micro-leakage.

It would be desirable to develop an improved root canal filling cone that lend itself to mass production, and a manufacturing process for high throughput production of root canal filling cones.

SUMMARY OF THE INVENTION

The present invention provides an improved root canal filling point/cone that can be manufactured precisely to result in better obturation with less micro-leakage.

One aspect of the present invention is directed to a molded root canal filling point. Another aspect of the present invention is directed to a thermo-pressure molding process for manufacturing root canal filling appliances (e.g., Gutta Percha points). Another aspect of the present invention is directed to the structure of the mold for undertaking thermo-injection molding. A further aspect of the present invention is directed to a production line comprising the thermo-injection process.

The present invention will be described herein-below in reference to root canal filling points made of endodontic filler material including what is known as Gutta Percha, for example. However it is understood that the present invention could be applied to manufacturing root canal filling points based on other types of endodontic filler materials, currently known or future discovered, without departing from the scope and spirit of the present invention.

BRIEF DESCRIPTION OF THE DRAWINGS

For a fuller understanding of the nature and advantages of the invention, as well as the preferred mode of use, reference should be made to the following detailed description read in conjunction with the accompanying drawings. In the following drawings, like reference numerals designate like or similar parts throughout the drawings.

FIG. 1A is a schematic illustration of a root canal filing cone in accordance with one embodiment of the present invention; FIG. 1B is an orthogonal view of FIG. 1A.

FIG. 2A is a schematic perspective view of a mold block in accordance with one embodiment of the present invention; FIG. 2B is a side view of the mold block of FIG. 2A; FIG. 2C is an end view orthogonal to the side view of FIG. 2B; and FIG. 2D is a sectional view illustrating the wall profile of a mold cavity.

FIG. 3A is a schematic perspective view of a mold block in accordance with another embodiment of the present invention; FIG. 3B is an end view of FIG. 3A.

FIG. 4A is a schematic perspective view of a mold base in accordance with one embodiment of the present invention; FIG. 4B is a sectional view taken along line B-B in FIG. 4A; and FIG. 4C is a sectional view taken along line C-C in FIG. 4A.

FIG. 5 is a diagrammatic view of a thermo-injection mold system in accordance with one embodiment of the present invention.

DETAILED DESCRIPTION OF THE PREFERRED EMBODIMENTS

Figure 6:
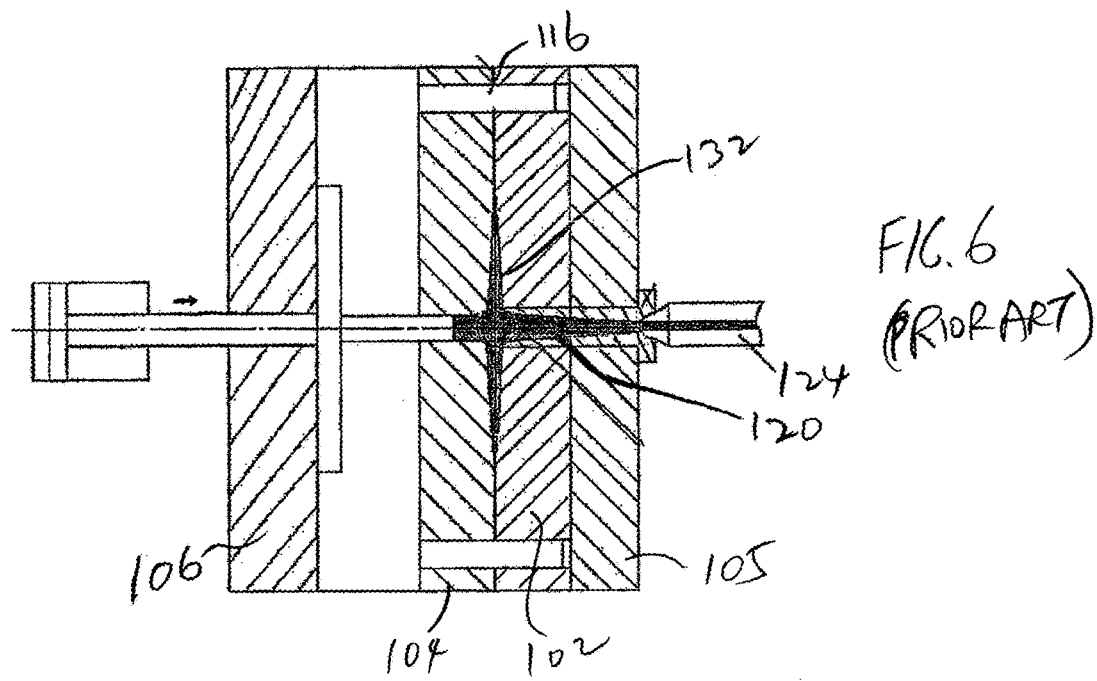
FIG. 6 is a schematic sectional view illustrating a prior art split mold.

This invention is described below in reference to various embodiments with reference to the figures. While this invention is described in terms of the best mode for achieving this invention's objectives, it will be appreciated by those skilled in the art that variations may be accomplished in view of these teachings without deviating from the spirit or scope of the invention.

The present invention provides an improved root canal filling point/cone that can be manufactured precisely to result in better obturation with less micro-leakage. One aspect of the present invention is directed to a molded root canal filling point. Another aspect of the present invention is directed to a thermo-pressure molding process for manufacturing root canal filling appliances (e.g., Gutta Percha points). Another aspect of the present invention is directed to the structure of the mold for undertaking thermo-injection molding. A further aspect of the present invention is directed to a production line comprising the thermo-injection process.

The present invention will be described herein-below in reference to root canal filling points made of endodontic filler material including what is known as Gutta Percha, for example. However it is understood that the present invention could be applied to manufacturing root canal filling points based on other types of endodontic filler materials, currently known or future discovered, without departing from the scope and spirit of the present invention.

FIG. 1 illustrates a dental root canal filling cone (or point) 10 in accordance with one embodiment of the present invention. The cone 10 comprises a generally conical body 12 comprising a heat flowable material, such as Gutta Percha. The cone body 12 has a thick or large end 13 and a tapered thin or small end 16, which has a taper angle 15 that fits in the apex end of a prepared root canal cavity (the taper angle at the apex of the cavity being defined using a file tool known in the dentistry field). The diameter of each diametric section along the longitudinal axis of the body 12 is substantially circular, up to the large end 13. Extending beyond the large end 13 is a flat tab 18. An identification indicia 19 (e.g., alphanumeric) may be provided on the flat surface of the tab 18, to facilitate the user (dentist) to distinguish the particular configuration of the cone 10 (e.g., the indicia corresponds to a particular size, taper angle, material, etc.). During a dental root canal treatment process, the cone body 12 is inserted into the prepared root canal cavity. The tab 18 (along with excessive section of the body 12 that is not needed) can be removed by cutting before or after insertion. Heat is applied to the large end 13 using a heating tool (e.g., a heat gun). As the Gutta Percha material softens under the applied heat, the material flows in the root canal cavity to fill the root canal. Ideally, sufficient heat reaches the small end 16 of the cone 10 to flow the material to completely fill the apex of the root canal cavity.

The general dimensions of the cone 12 may be within the following ranges, for example:
- a. Overall length L of cone 10: between 20 to 50 mm; or preferably between 25 to 35 mm.
- b. Diameter of the small tip end 16: between 0.01 to 0.3 mm; or preferably between 0.01 to 1.8 mm.
- c. Diameter of the large end 13: between 0.5 to 5 mm; or preferably between 0.8 to 2.5 mm.
- d. Taper angle: between 2° to 15°; or preferably between 5° to 12°.
- e. Length F of tab 18: between 3 to 5 mm; or preferably between 1.5 to 3.5 mm.
- f. Thickness H of tab 18: between 0.5 to 3 mm; or preferably between 0.8 to 2.8 mm.

In accordance with the present invention, the cone 12 is made by molding, and in particular a thermo-pressure molding process, such as a thermo-injection molding process. The molding process of the present invention produces cones having good dimension control, within tight/small tolerances, such as ±0.01 mm.

In accordance with one embodiment of the present invention, the thermo-injection molding system 20 is schematically illustrated by reference to FIG. 5. The primary components in the thermo-injection molding system 20 is the mold 22, which dictates the molding process parameters using such mold. The injection molding system 20 further includes injector 24, vacuum pump 26, compressed air source 27 and coolant (e.g., water) pump 28, as will be discussed in greater detail below.

FIGS. 2A-2D are schematic diagrams of a mold 22 in accordance with one embodiment of the present invention. The mold 22 has a body that is generally in the form of a block of material (hereinafter referred to as mold block 22) that includes one or more mold cavities 32 defined therein having shape, dimensions and taper conforming to those of desired Gutta Percha points to be molded. For example, a bigger mold block can have multiple mold cavities in a particular array and smaller mold block can have just a single mold cavities. A particular mold block 22 may be provided with mold cavities having the same shape, dimensions and taper, or different shapes, dimensions and/or taper. FIGS. 3A and 3B schematically illustrates a mold block 22' in accordance with another embodiment of the present invention, which has two rows of mold cavities 32, with modified water cooling (which will be explained later below).

The mold cavities 32 are generally in a conical shape, with a larger open end at one surface of the mold block, and a smaller open end at an opposite surface of the mold block. The wall profile configuration at the larger open end of each mold cavity 32 is more clearly shown in FIG. 2D. The larger end of a conical mold cavity 32 is flared, with two short taper sections 34 and 35 in series, having different taper angles that are progressively larger than the taper angle of the mold cavity 32. The first taper section 34 (e.g., 2 mm in length) extends from the end of the conical mold cavity (e.g., 30 mm in length), and the second taper section 35 (e.g., 2 mm in length) extends from the end of the first taper section 34 and terminates at the surface of the mold block 22. The second taper section 35 is shaped and sized to receive and seat the nozzle of the mold injector 24, and the first taper section 34 provides a space for absorbing back flow pressure when injecting material into the cavity 32.

The mold block 22 may be made of commonly used mold making material, semi-soft or rigid, such as flexible rubber based compound, metal (e.g., stainless steel, titanium), resin based material (e.g., crystal acrylic) and composite, etc. For certain molded points and/or injection process, clear transparent acrylic resin provides a material that is less expensive and easy to work with to form the mold cavities.

The mold cavities 32 may be formed by precision machining (e.g., drilling using a bit or laser, etc.), or by a reduction molding process (i.e., first making Gutta Percha point replicas with surgical steel or Titanium, then using these replicas to make a reduction mold block). The mold block 22 thus has through-and-through conical channels, which conforms to the precise shape, dimensions and taper angle of desired Gutta Percha points to be molded. In forming the mold cavities 32, appropriate clearance/tolerance is provided to take in consideration any temperature induced slight dimension changes for the molded pieces, so as to obtain accurate final dimension. Referring also to FIG. 5, generally, the overall length of the conical mold cavities is on the order of about 30 mm (not include tapers at the larger end, described below). For example, the taper angle may be 2 to 12 degrees. The diameter of the smaller end of the cavity is about 0.15 to 1.8 mm, and the diameter of the larger end of the cavity is about 0.50 to 2.0 mm.

For the mold blocks shown in FIGS. 2 and 3, each mold block is provided with temperature control to control the softness and hardness of Gutta Percha material during the molding process. In the illustrated embodiment of FIG. 2, fluid conduits or channels 36 are provided in the mold block 22 for passage of heating or cooling fluid (liquid or gas) to control the temperature of the mold block. For example, straight 5.0 mm diameter water channels 36 are provided to allow circulation of hot or cold water there-through. While only two channels 36 are schematically shown in the embodiment of FIG. 2, additional channels 36 may be provided. Water (or other cooling fluid, gas or liquid) may be fed directly into the channels 36, or a tube or pipe may be inserted into each channel 36 and water is feed into the tube or pipe. This may facilitate connection of water source and drain to the ends of the pipe. Further, instead of straight fluid channels, the fluid channels may serpentine in the block or be in a network of channels to provide a more even temperature control coverage. Other means of temperature control may be provided (e.g., Peltier heating/cooling).

While in the embodiment illustrated in FIG. 2 (and FIG. 3 as well), the mold block 22 shown has a monolithic body having integrated water cooling/heating channels, the mold block 22 may instead comprise two or more parts that are assembled together, without departing from the scope and spirit of the present invention. Further, instead of having integrated water cooling/heating channels running through the mold block 22, cooling/heating elements (e.g., temperature controlled tubes or other heat exchangers) may be attached to or engaged at the outside of the mold block, as shown in the embodiment of FIG. 3. In the embodiment as illustrated in FIG. 3, the mold block 22' comprises two rows of mold cavities 32 and open channels 36' along the sides of the mold block 22' for receiving water tubes/pipes 37 for heating/cooling of the mold block 22'. The water pipes/tubes 37 may be held securely in the open channels 36' on the sides of the mold block 22' by a clamp, or a suitable holding mechanism (not shown). This presents a simple, quick release heating/cooling configuration, with relatively low maintenance.

Referring to FIG. 5, other components in the novel injection molding system 20 include a vacuum unit 26, a mold injector 24, a compressed air source 27, a low-flow (e.g., 2 cfm) water circulating pump 28 and associated plumbing to circulate hot and/or cold water to and from the mold block 22. The production line consists of three primary stations I, II and III, as schematically shown in FIG. 5. The production process is described below in reference to the mold blocks illustrated in the embodiments of FIGS. 2 and 3 (collectively schematically shown as mold block 22 in FIG. 5, and individually referred in reference to the embodiments of FIGS. 2 and 3).

The first station I is the mold block preparation station, at which the cavities 32 in the mold block is cleaned with compress air, and lubricated with a thin, light liquid mineral oil.

The second station II includes an injection molding machine (e.g., Sanyo, STI4,0-400VS). There is a base 23 that supports the mold block 22. The structures of the mold block 22 and base 23 are more clearly illustrated in FIG. 4. For a mold block having the structure of the mold block 22' in the embodiment of FIG. 3 is used, the water pipes/tubes 37 in the open channels 26' on the sides of the mold block 22' would be above the top of the base 23, as schematically illustrated in the embodiment of FIG. 5. A spring bias (not shown) may be provided on the top of the base 23, to apply a bias on the water pipes/tubes against the open channels on the side of the mold block. Alternatively (not shown), the open channels 36' could be provided at a height on the mold block 22' such that when the mold block 22' is seated onto the base 23, the water pipe/tubes 37 would be sandwiched in a space between the mold block 22 and the inside wall of the top portion of the base 23 to provide a good positive thermal contact between the water pipes/tubes 37 and the mold block 22'.

Referring to FIGS. 4B, the base 23 has a recess 39 defined therein, which receives the bottom portion of the mold block 22. The recess 39 in the base 23 extends below the bottom of the mold block 22, to form an air plenum 38 after the mold block 22 is seated into the recess of the base 23 (a gasket, not shown, may be provided between the bottom surface of the mold block 22 and the top surface of the flange 33 in the base 23). The plenum 38 is connected to a vacuum pump 26 via conduits 31 through the end sides of the base 23. With the mold block 22 seated on the base 23, the vacuum pump 26 is first turned on to clean/suck out any excess mineral oil. With the vacuum pump 26 running, the mold injector nozzle 24 is lowered to seat against the larger taper section 35 in a mold cavity 32 in the mold block 22. The injector 24 starts to inject heated and softened Gutta Percha material into the mold cavity 32 in the mold block. While FIG. 5 shows a single injector nozzle, preferably there is an array of injector nozzles matching the array of mold cavities in the mold block 22, so that all the mold cavities can be filled with material at the same time. Otherwise, an injector 24 (or a group of injectors) can be controlled to inject material into each cavity 32 (or each group of cavities) in sequence.

A little excess material would emerge from the smaller open ends of the mold cavities. As this excess material emerge from the opening into the plenum 38, the circulation of air suction in the plenum 38 cools and hardens the excess material. Excess material is not expected to be fed to the vacuum lines, but a filter may be provided to block potential lose material from clogging the vacuum lines. Alternatively, instead of running the vacuum pump during injection, injection may be carried out without the vacuum pump, but the plenum 38 may need to be bled during injection.

Instead of providing cooling tubes on the sides of the mold block 22', cooling may be provided by the base. For example, a mold block may be inserted into a base having a block that is provided with a network of fluid channels (not shown in FIG. 5) for circulating hot and cold fluid (e.g., water). In this embodiment, the mold block having the mold cavities can be made with high precision, but the base block having the fluid channels could be made with significantly low precision at significantly lower costs, without affecting the tolerance of the finished molded pieces. The base block containing plumbing may be readily replaced when it becomes corroded, clogged, or otherwise damaged by the circulating fluid, without having to replace the more expensive mold block.

For temperature control, hot water (e.g., at 80 to 90 degrees C.) is fed through the water pipes/channels 37 to heat the mold block 22 during the entire mold injection process to facilitate smooth flow of Gutta Percha material. Once the injection process has completed, cold water (e.g., at 6 to 10 degrees C.) is fed through the pipes/fluid channels 37 to cool the mold block 22 so as to cool off the Gutta Percha material inside the mold block. After the Gutta Percha material cool off sufficiently, the mold block 22 is moved to the third station II.

The third station III has a similar base 23' as the base 23 at the second station II for receiving the mold block 22. The base 23' is connected to a source of pressurized air instead. Before seating the mold block 22 into the base 23', any excess material emerged from the bottom (small) end of the mold cavities is removed (e.g., with a sharp razor blade), to form a very sharp flat tip end of the molded filler points 10. Then the mold block 22 with Gutta Percha points 10 inside the mold cavities 32 is seated onto the base 23' to form the plenum 38'. Pressurized air is applied to the plenum 38' (e.g., from an air compressor 27 or compressed air reservoir) below the bottom of the mold block 22 to loosen up and push out the Gutta Percha points 10 already molded inside the mold cavities 32.

Alternatively, the functions of the second station II and third station III may be integrated at the same station. Vacuum and pressurized air may be alternatively applied to the plenum in sequence via the same lines in the base, using appropriate valves to divert vacuum and pressurized air, or via separate, dedicated vacuum and pressurized air lines in the base.

There are several advantages of the inventive molding process to make the Gutta Percha points 10. One advantage is that it will take human hands out of the rolling process to eliminate the risk of contaminants being incorporated into the final products—Gutta Percha points 10. Second advantage is that the dimension of all points 10 will be uniform and more precisely matching the size and shape of corresponding root canal cavities formed by shaping instruments (i.e., files) used to shape the root canal cavities in the patients jaw just prior to inserting the Gutta Percha points. Third advantage is that all points are made through this process are denser in texture, therefore less likely for possible air bubbles to form inside the points, so better final seal of the root canal cavities. Further advantages may be realized when the manufacturing production line can be carried out in a fully automated manner, by controlling automatic processing and placement of the mold block from one station to another.

While the foregoing description discussed single point mold cavities, it is understood that root canal filling points having multiple connected points can be molded by injection molding without departing from the scope and spirit of the present invention. Appropriate mold cavities may be defined in a mold block to mold root canal filler cones each having multi-points in desired configuration between points (e.g., each point having same or different taper angles).

In an alternate embodiment, the mold block comprises two half-blocks, and an improved thermo-injection molding process. Once again, the present invention will be described herein-below in reference to root canal filling points made with endodontic filler material including what is commonly known as dental Gutta Percha. However it is understood that the present invention could be applied to manufacturing root canal filling points based on other types of endodontic filler material, currently know or future discovered such as metallic, organic, inorganic based thermo-conducting material, without departing from the scope and spirit of the present invention.

The earlier described embodiment of the mold design has molding cavities in e.g., vertical orientation in one piece of mold plastic or steel block. Those cavities are tapered in shape to produce tapered Gutta Percha points for various dental clinical applications. The smaller end of a Gutta Percha point can have diameter of 0.10 mm or less. When separating, "pulling" these Gutta Percha points out of the mold cavities. It has been found that for points with small end tips less than 0.4 mm diameter, there is too much resistance/traction, which require higher pulling/separating force. As a result, those points often get deformed/elongated after separated from the mold cavity. This problem gets even worse when Gutta Percha points require more than one taper along the length, which is commonly called multi-taper Gutta Percha points. For example, a Gutta Percha points can have 8 degree taper from small tip end up to 5 mm from it and 5 degree taper from that 5 mm point all the way to the bigger end of the Gutta Percha point. Traditionally, dental clinicians call a Gutta Percha points with single taper design continuous taper Gutta Percha points. Making multi-tapered mold cavity in the vertical orientation mold is extremely difficult as well. In summary, single piece vertically oriented mold design is successful for larger sized continuous taper Gutta Percha points. But for producing smaller sized Gutta Percha points, especially multi-taper Gutta Percha points, a different approach would be more desirable.

The new mold design is directed to molding using two complementary mold halves that together define mold cavities for dental root canal filler points/cones (i.e., using split mold). After the two mold halves of the above described split mold is pressed together, Gutta Percha material is injected into the mold cavities, cooled to set the material, the mold halves are separated, and the molded piece is released from the retaining mold halve by pushing the piece out of the mold cavity (e.g., using push rod 61 shown in FIG. 7B).

Figure 7A:
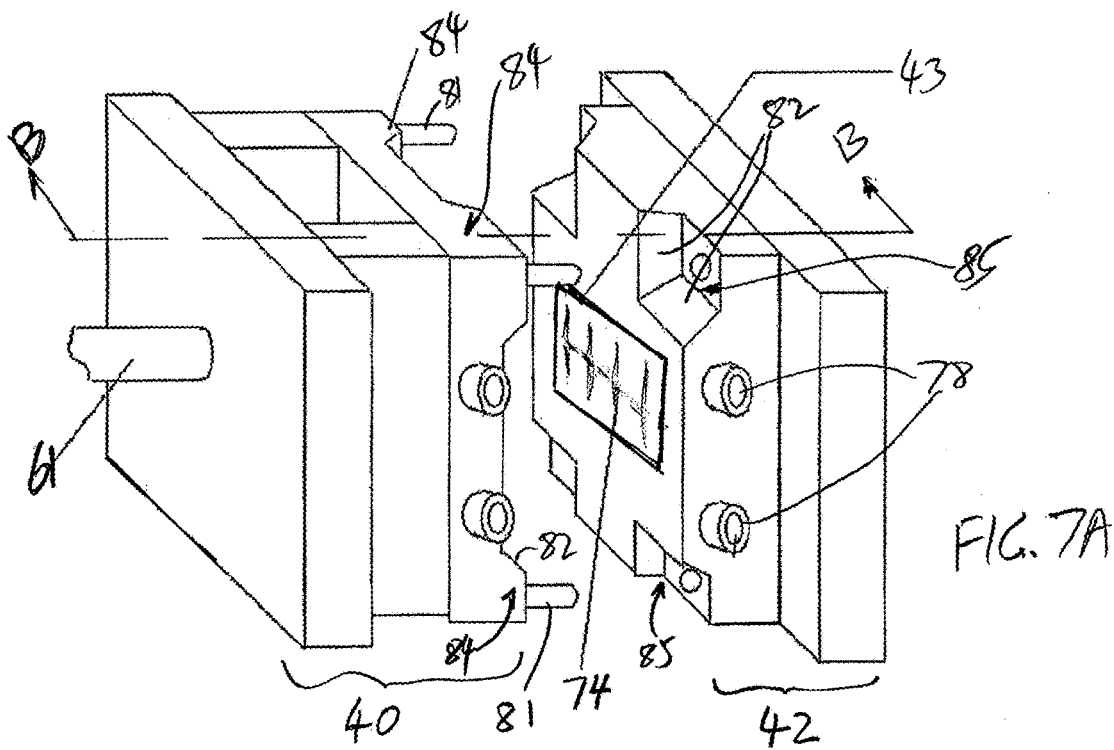
FIG. 7A is a schematic perspective view illustrating a split mold in accordance with one embodiment of the present invention.
Figure 7B:
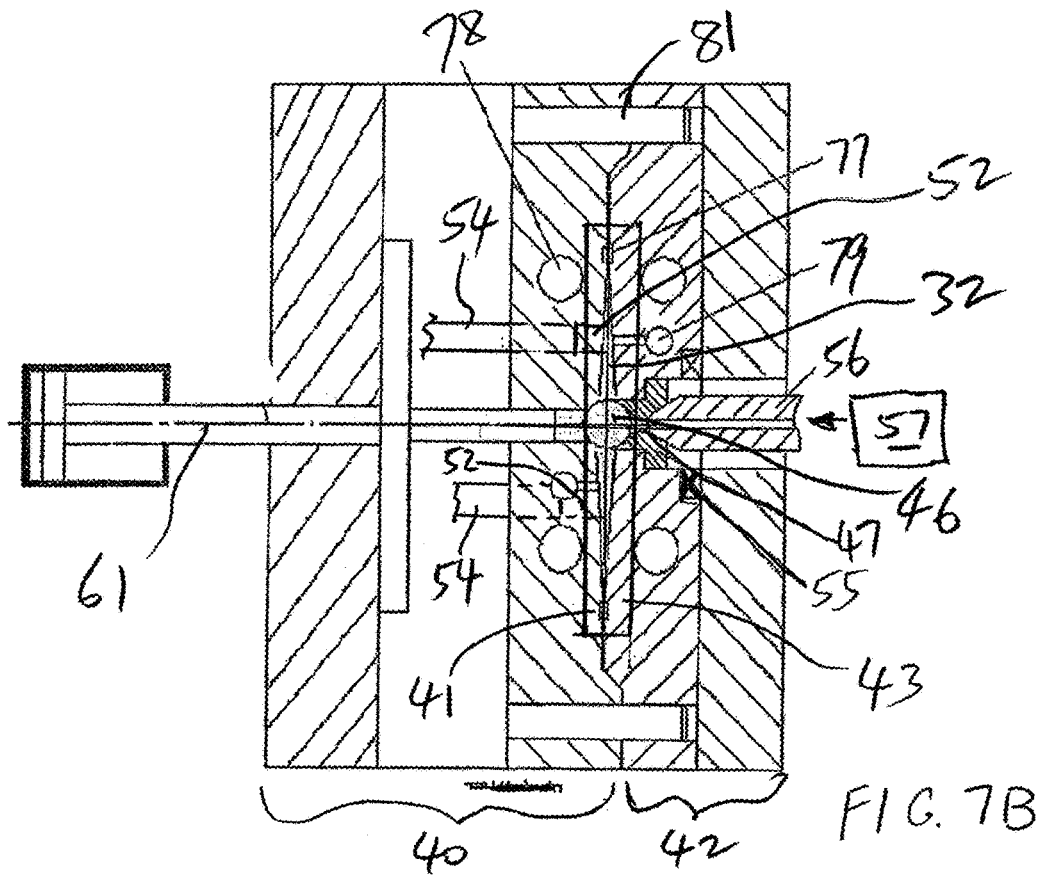
FIG. 7B is a schematic sectional view taken along line B-B in FIG. 7A.
Figure 7C:
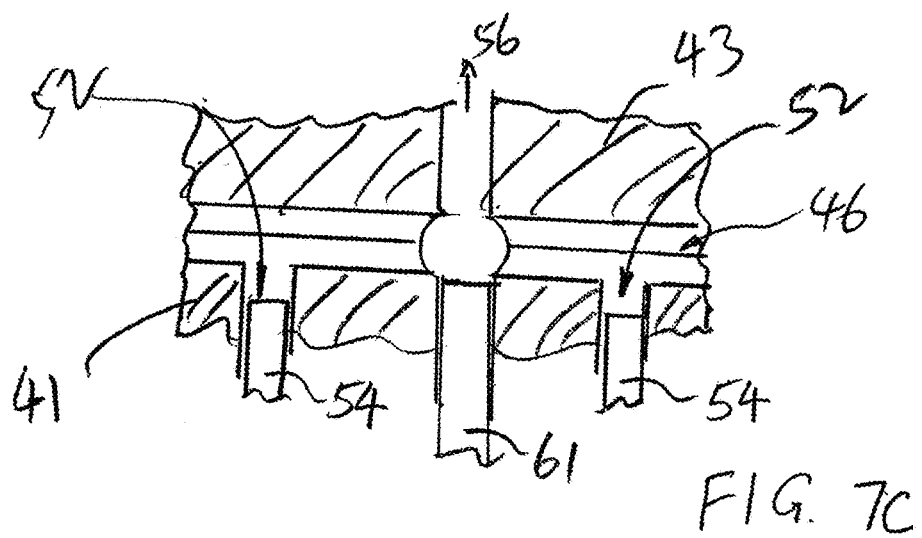
FIG. 7C is an exploded sectional view.
Figure 10:
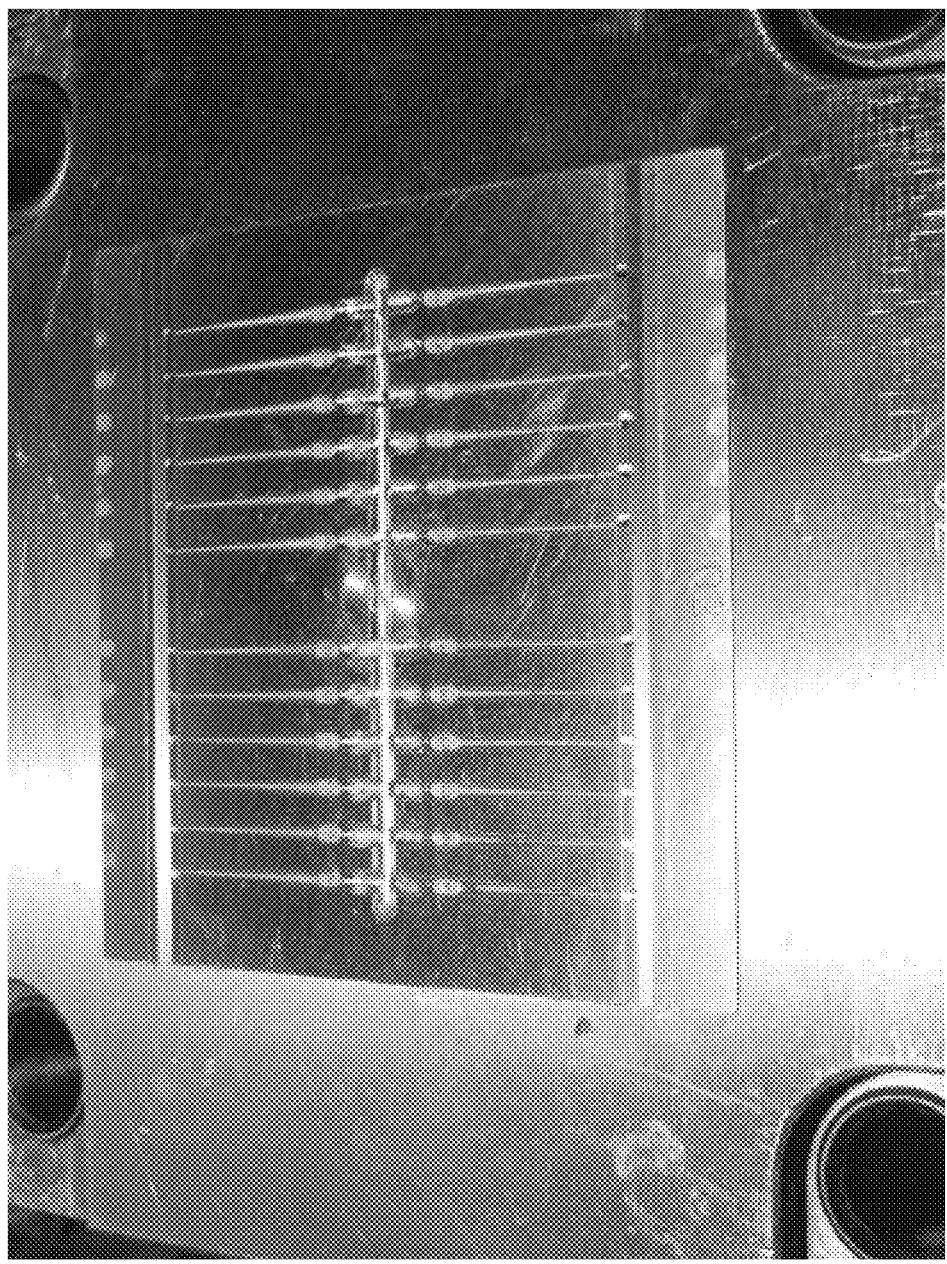
FIG. 10 is a photograph image of a mold halve of a split mold, in accordance with one embodiment of the present invention.
Figure 11:
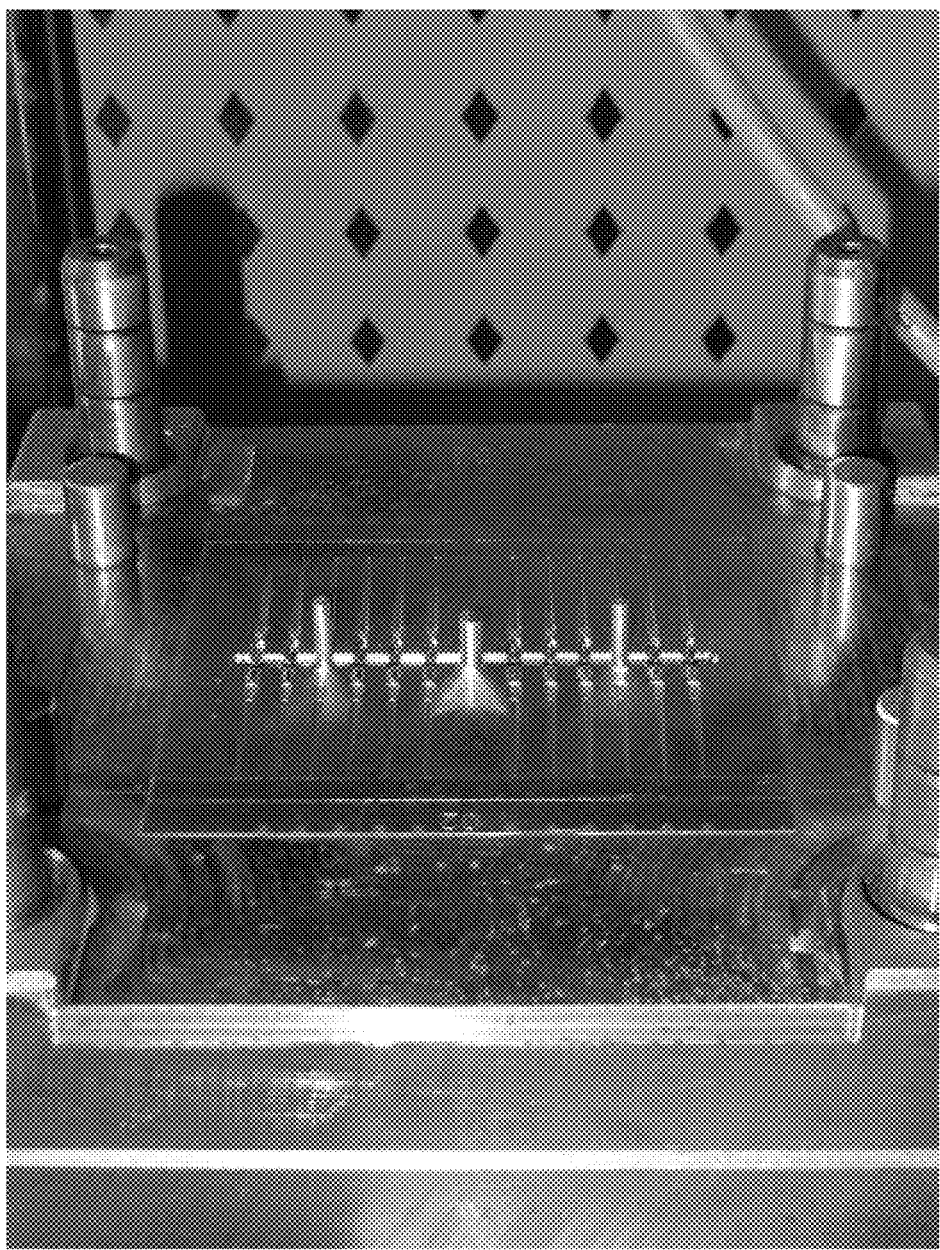
FIG. 11 is a photograph image of a matching mold halve of a split mold, in accordance with one embodiment of the present invention.

FIGS. 7A-7C illustrate one embodiment of the inventive spilt mold. The molding process involves linear movements (e.g., lateral/horizontal, or vertical) of a two-part mold (which is commonly called the split mold) to separate and close opposing mating mold halves 40 and 42 (i.e., the mold halves are moved laterally/horizontally or vertically with respect to each other, such that the complementary molding cavity surfaces of the opposing mold halves move towards and away from each other to close or separate the two mold halves). Each move halve (40, 42) includes a frame (70, 72) supporting in a central region a mold core halve (41, 43) that defines a mold chamber 74 having a surface profile that conforms to half of a tapered cone 10 (i.e., a cone is split along its sagittal plane, which lies in the longitudinal direction of the cone and along the axis of the cone), and is a substantially identical halve of a complete mold cavity 32 that conforms to a tapered cone 10. One of the mold halves may be stationary and fixed in place, and the other mold halves is supported for movement with respect to the fixed mold halve. The two mold halves 40 and 42 open and close with respect to each other along the sagittal plane of the molded Gutta Percha points. This makes it easier to separate the finished molded Gutta Percha cones 10 from a mold halve, and with minimal or without significant distortion of the cone. FIG. 11 is a photograph of a mold halve that is stationary in the injection molding system, in accordance with one embodiment of the present invention. FIG. 10 is a photograph of a mold halve that is moved with respect to the mold halve shown in FIG. 11, in accordance with one embodiment of the present invention.

Heretofore, inventors are not aware of any Gutta Percha cones made by injection molding. In developing molded Gutta Percha points, the inventors explored conventional split mold designs and plastic injection molding processes. Referring to FIG. 6, a conventional split mold 100 has two mold halves 102 and 104 supported by frames 105 and 106. Each split mold halve 102/104 has a chamber defining the surface profile of part of the final injection product to be molded. The two halves 102 and 104 close together to make a full mold cavity 132. Pins 116 are provided for aligning the mold halves 102 and 104. One mold halve can be fixedly supported in the mold injection machine and the other mold halve is supported to move along a track with respect to the fixed mold halve, to open and close the mold. For material injection, an injection nozzle 124 is butted against the outside of the mold frame 105, and material is injected into and through a rather long injection opening pathway 120, before the material reaching the mold cavity 132.

The inventors realized that conventional split mold designs and plastic injection processes are not compatible with making Gutta Percha cones. The inventors found that conventional plastic injection molding machines, without modification in accordance with the present invention, would not be able to mold dental Gutta Percha cones due to the inherent nature of dental Gutta Percha material and the characteristics of conventional molding process not being compatible for Gutta Percha material. Split mold injection manufacturing process that were developed and used in plastic industry were designed to handle plastic materials that general have very high flow characteristic and melts at relatively low temperature. Because of the high stickiness/low flow character of dental Gutta Percha, extreme small dimension (can be as small as 0.10 mm tip diameter) of the desired products and very tight tolerance of the dimension are required. For example, for root canal filling, the Gutta Percha cones should not have significant residual mold lines (excessive material creeping from the mold cavity into the interface between a two-part mold, which remains on the cone after molding). In accordance with the present invention, conventional injection molding machine is adapted but must be modified with the inventive mold design and injection molding process in order to be able to conduct injection molding to obtain useful Gutta Percha cones of acceptable quality.

In summary, the inventors created a novel mold design and injection molding process by considering and overcoming the following issues particular to Gutta Percha material, so as to overcome the challenges of injection molding Gutta Percha cones:

1. Dental Gutta Percha material has low melting temperature and poor flow ability, which makes it difficult to fill entire mold cavity to form an ideal shaped product.

2. Because of low melting temperature of dental Gutta Percha, the residual elevated temperature inside metal mold chamber prevents Gutta Percha from hardening fast enough for a successful mold separation without Gutta Percha cone distortion.

3. Dental Gutta Percha has some stickiness when softened up, which makes it not being a very desirable material for plastic mold injection machine.

4. Dental Gutta Percha cone requires precision dimension for clinical use. The conventional plastic mold injection machine and mold design often leaves a rather large mold line which would not meet the precision required for dental Gutta Percha cone.

5. Because of dental Gutta Percha's low melting point and lack of flowability, higher temperature and higher pressure are required to extrude and inject Gutta Percha into a mold cavity. This often results in the permanent molecular changes inside dental Gutta Percha compound.

To overcome all of the above mentioned challenges, various modifications have been implemented to improve a conventional plastic injection molding system to become suitable for injection molding dental Gutta Percha material. The improvements and features incorporated into the novel dental Gutta Percha injection mold structure and injection molding process are discussed below.

A. Features to improve Gutta Percha material flowability by designing a new mold injection pathway and temperature control system:

1. Using specially designed material heating/compaction chamber (injection cylinder 57) with high strength material and smaller diameter extrusion screw to increase extrusion pressure.

2. Removing injection opening pathway and shortened injection nozzle 56 to reduce injection resistance. It also helps in eventual mold separation process.

3. Adding heating ring around injection nozzle 55 to facilitate Gutta Percha flow into mold cavities 32.

4. Adding venting channels 77 at far (tip) end of mold cavities to vent air to reduce air resistance, therefore to improve Gutta Percha flowability into the mold cavities. The air vent channels are drilled a couple of microns deep groove in the surface and at an optimal angle so only air, not the dental Gutta Percha material, is escaping.

5. Incorporating hot/cold water circulating system 78 as part of the mold structure to preheat entire mold block for improved Gutta Percha flowability.

6. Changing mold internal injection secondary channels 46 angulation from main channel 47 (initial passage in mold receiving material from injection) to the final mold cavities 32 to reduce flow resistance.

B. Features to improve mold thermo conductivity to make Gutta Percha cool and harden faster to assist mold separation process:

1. Mold core halves (41, 43) are made of material with higher thermo conductivity to distribute heat faster in the internal region of the mold halves.

2. Redesigned mold internal hot/cold water circulating system. When running ice cold water through the mold block, Gutta Percha points get cold and harden faster for easier mold automatic separation.

C. Features to control Gutta Percha stickiness by reducing its surface tension to facilitate mold separation step:

1. Other than providing water circulating cooling, spray openings 79 are provided in the mold to spray separation lubricating agent into mold cavities to keep cavities clean and surface tension low. Therefore it will be easier to separate the cold without Gutta Percha points sticking to the mold cavity surface.

2. Removed traditional injection opening pathway to reduce contact surface area of residual molded material. The short main injection channel 47 minimizes the resistance when separating the mold.

D. Features to improve molded product precision, to avoid mold mismatching when closing, and to reduce/eliminate mold line:

1. To improve lateral alignment of the mold halves 40 and 42, other than locking/alignment pins (similar to the alignment pins 116 in FIG. 6) provided in conventional plastic injection mold machines, protrusions 84 and indents 85 having beveled mating surfaces 82 are provided to form gear shaped locking platforms between the mold halves 40 and 42 to improve alignment and locking of the mold halves. Specifically, one mold halve (e.g., mold halve 40 as shown) is provided with protrusions 84 with a flat top and/or indents with a flat bottom, with a beveled surface 82 extending from the flat top of the protrusions 84 and the flat bottom of the indents 83. The other mold halve is provided with matching indents and/or protrusions, with similar flat top/bottom and beveled surface. When the mold halves close and mate under pressure, the matching protrusions and indents will slowly "bite" or "grip" into each other to lock the two mold halves in precise lateral alignment across the plane of the mold cavities, so as to form mold cavities to meet the dimension of Gutta Percha point with sufficient precision suitable for clinical use. Alternatively, the mating surfaces of the mold halves may be planar without the bevels, but the bevels provide improved lateral alignment to result in mold pieces with improved results as noted above.

2. Increased thickness of the mold frames 70 and 72, and subject the mold frames to high temperature treatment. This increases its strength and reduce deformation when pressure is applied to lock the mold halves together.

3. Internal surfaces of mold cavities 32 are treated with Nitrogen to increase surface hardness and/or strength, thus reducing wear. This ensures the integrity of the mold cavities to allow for precision closing of the mold cavities using the mold halves, to minimize and substantially eliminate residual mold line on the molded pieces.

4. Providing a cold water circulating system to cooling channels 78 to quickly reduce mold body temperature to minimize thermo expansion from repeated mold injection operation.

E. Features and process protocols implemented in injection molding machine to provide correct technical references specific for dental Gutta Percha material to protect its molecular stability and its properties for clinical applications:

1. Reducing the holding volume of the heating/compacting chamber or injection cylinder 57 for preparing the final Gutta Percha material ready before injection. This minimizes the length of time for Gutta Percha material to remain inside a high temperature and high pressure chamber to avoid possible changes to its molecular structure.

2. The holding/compacting chamber or injection cylinder 57 has several heating zones (e.g., three to five zones) to gradually increase the temperature of Gutta Percha material to its melting point as it is moved towards the injector 56. This further prevents breakdown of Gutta Percha molecular structure.

In accordance with the present invention, the Gutta Percha points made by the novel Gutta Percha injection molding system has improved tolerance and quality that meet the requirements for clinical use. Manufacturing efficiency is improved, reducing production costs. The molded pieces and associated injection molding process can also mark ISO size codes onto each individual Gutta Percha point to reduce the chance of dentist error in picking a wrong size/shape Gutta Percha point. Manual hand-rolled Gutta Percha points cannot include this safety feature. The novel Gutta Percha injection molding system can also produce Gutta Percha points with multi-tapers on a single point. This will satisfy clinicians' needs to have multi-tapered Gutta Percha points to match the new generation of multi-tapered root canal cleaning instruments/files. Many manufacturers have tried for many years using manual hand rolling technique to produce multi-tapered Gutta Percha points, but without any success.

In accordance with the present invention, given the design of the mold and molding process, the mold remains in the injection molding machine without moving between stations, as was in the earlier embodiment. Mold cleaning and preparation are easier to undertake more frequently.

The clinical aspect of root canal treatment techniques and material are evolving rapidly. Using the novel mold design and injection molding technology, challenges encountered by dental clinicians have been meet. The novel injection molding system can be adapted to evolve with new clinical challenges in dentistry.

Figure 9:
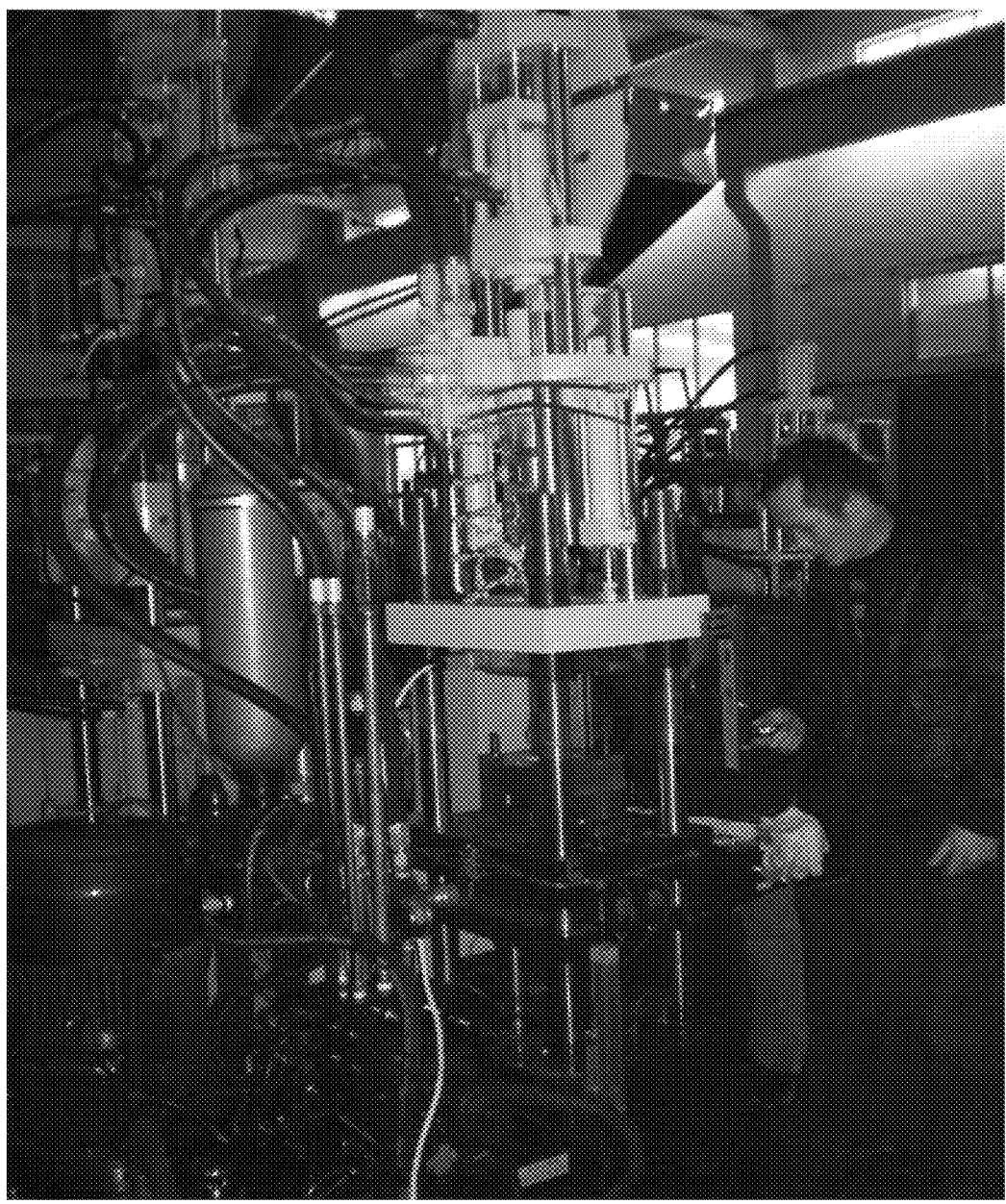
FIG. 9 is a photograph image of a vertical injection molding system, in accordance with one embodiment of the present invention.

While the above embodiment illustrated in the drawings refers to mold halves supported for horizontal movements in an injection molding machine, it is contemplated that the mold halves can be supported for vertical movements in another injection molding machine, without departing from the scope and spirit of the present invention. FIG. 9 is a photograph of a vertical injection molding system incorporating the features discussed above and below in accordance with another embodiment of the present invention.

Below are further elaborations of further improvements to the injection molding system.

Dental Gutta Percha material requires much higher pressure to inject into the mold than plastic material. This requires even tighter closing of the split mold, to ensure tight mating of the mold core halves to tightly define a mold cavity. Instead of just increasing split mold locking pressure, the mold is designed such that instead of having each mold core halve supported in its respective frame with the surface of the mold core halve flush with the surface of the frame, the mold core halve is raised a few microns with respect to the surround surface of the frame, so that the mating surface of the mold core halve protrudes above the adjacent surface of the frame. When two halves of the mold close and lock together, the mold core halves will close much tighter to ensure a complete injection of the dental Gutta Percha material with better tolerance.

To increase the injection pressure inside the cavity chamber, the diameters of the network of secondary injection channels 46 (the channels in the plane of the mold cavities) leading to the mold cavities 32 are reduced. This will allow Gutta Percha material to build up extra pressure before bursting into the cavity chamber through those reduced diameter secondary channels 46. The main injection channel in line with the injection nozzle is shortened to reduce resistance and to save expensive dental Gutta Percha material. The injection speed of the Gutta Percha material, which dictates the travel speed of the material into the mold cavities, is important to a perfect Gutta Percha cone finish.

To increase the dental Gutta Percha material flow rate, an electrical heating element is provided in the form of a ring inside the mold supporting frame where the injection nozzle meet the mold core at the main injection channel opening. This will ensure the Gutta Percha material stays hot and liquid stage when entering into the cavity chamber. The cooling channels provided in the supporting mold frame help cooling off the mold quickly after a successful injection. The length of the injection nozzle is kept to a minimum and made "fatter" to better retain heat from the heating ring.

Figure 8A:
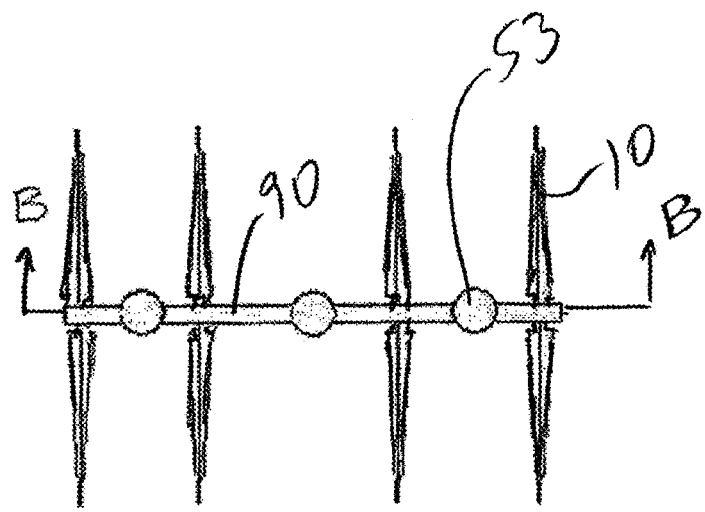
FIG. 8A is a schematic top view of a rack of molded cones, in accordance with one embodiment of the present invention.
Figure 8B:
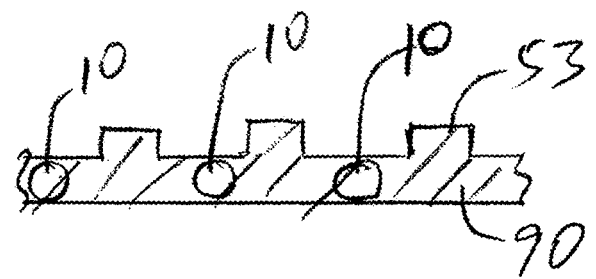
FIG. 8B is a schematic sectional view taken along line B-B in FIG. 8A.
Figure 8C:
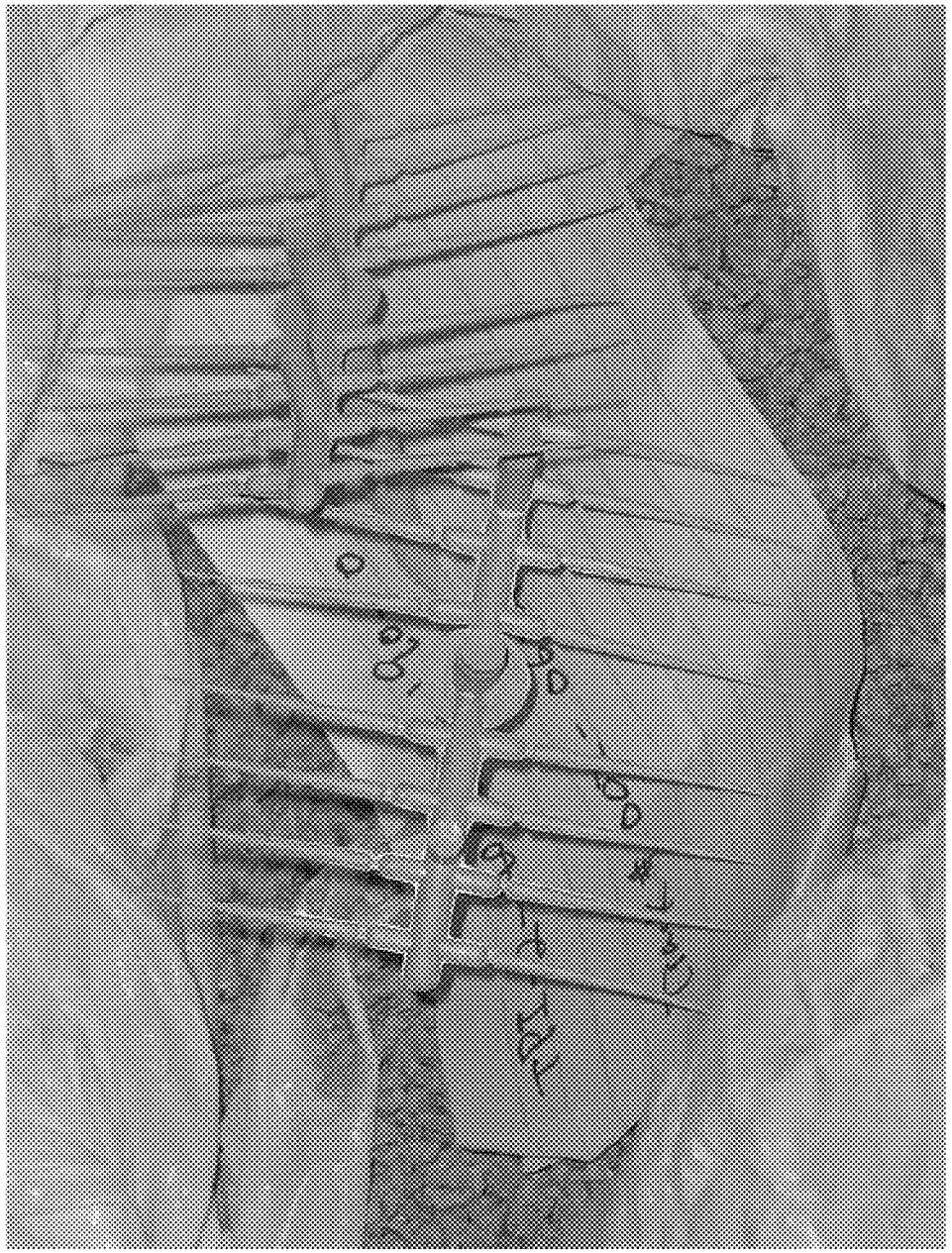
FIG. 8C is a photograph image of a top view of a rack of injection molded cones, in accordance with one embodiment of the present invention.
Figure 8D:
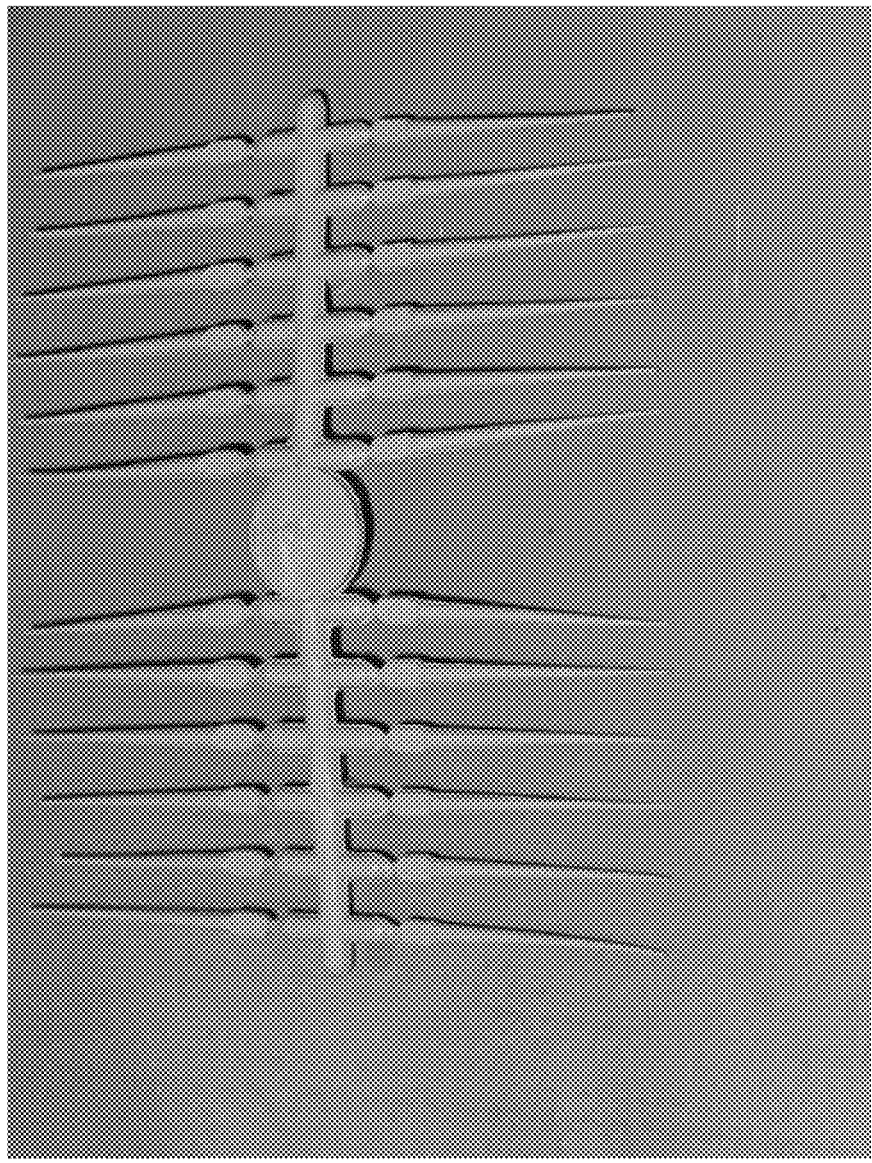
FIG. 8D is a photograph image of the underside of a rack of cones, in accordance with another embodiment of the present invention.
Figure 12:
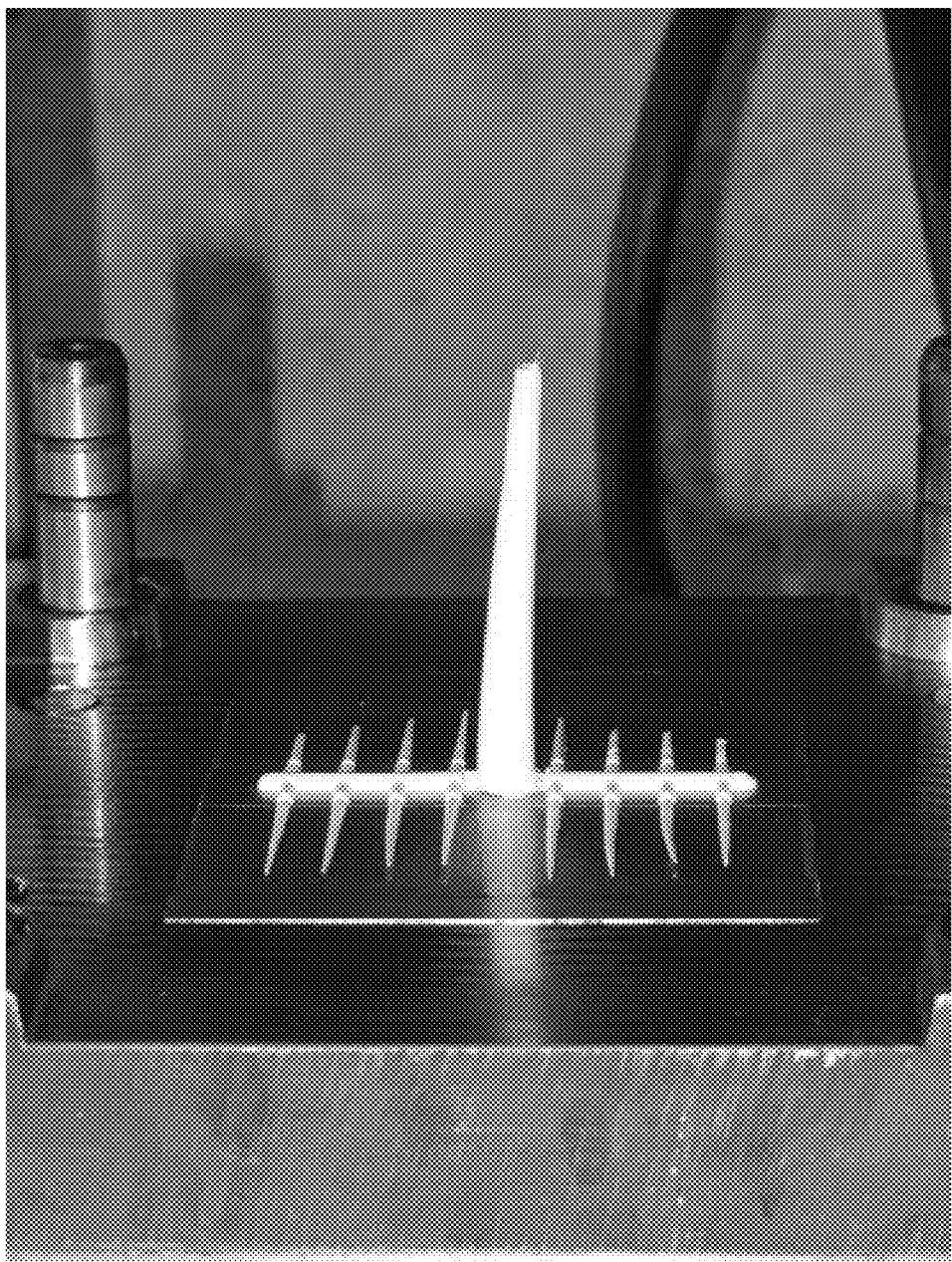
FIG. 12 is a photograph image of a rack of injection molded cones, in accordance with one embodiment of the present invention.

Referring to FIGS. 8A to 8D, the top view and a sectional view of the structure of the overall molded structure is shown. The cones 10 are connected to a spine 90, resembling the shape of a rake, or a rack of cones 10. When separating the two mold halves after injection and cooling, one challenge was to retain all mold injected Gutta Percha cones 10 on one of the mold halves (e.g., the fixed mold halve 40), to avoid the pieces of cones 10 from being separated from the spine 90, so that all the cones 10 can be collected and moved together in a cluster. Stub openings 52 are provided in the stationary mold core half 41. These stub openings 52 are slight undercut from the secondary injection channel 46. Gutta Percha material will end up being injected into these stub openings 52 to form stubs 53. See also FIGS. 7B and 7C. After the cooling and mold separation, the Gutta Percha stubs 53 will hold the rack of Gutta Percha cones 10 on the mold core half 41. Metal push rods 54 are provided from behind the stub openings 52 to push the finished stub 53 from the mold core halve 41. FIG. 8C is a photograph showing the side of the rack structure having the stubs 53. FIG. 8D is a photograph showing the other side of the rack structure (of a different rack). FIG. 12 is a photograph showing a rack of cones remaining on the stationary mold halve after separation of the mold halves.

If Gutta Percha compound is kept inside pre-heating and injection compartment for too long, the Gutta Percha material will degrade. The size of pre-heating and injection cylinder is reduced in length and in diameter to hold less amount of Gutta Percha material and to increase injection pressure and speed. Heating stations in this cylinder is reduced from 5 to 3. The temperature setting for heating stations are set in a progressively decreasing manner, from injection nozzle to back end of the cylinder, e.g., at 140, 120, 90 Celsius degree, at the respective station.

Because it uses very small amount of Gutta Percha material for each injection batch, the drive screw in the injection cylinder 57 (the cylinder behind the injection nozzle 56, which holds the material ready to be injected) in the molding machine barely starts rotating to push the material to be injected, and hydraulic pressure barely builds up to the optimum level for injection, yet Gutta Percha material is already injected from cylinder into mold chamber. This results in incomplete mold injection and results in not fully filled mold cavities. To correct these problems, the "driving screw" inside the injection cylinder 57 is redesigned so it moves less amount of Gutta Percha material to the front (nozzle end) with more rotations of the screw. At same time, forward plunging motion is provided to axially push the screw to achieve very fast high pressure injection.

Another change for the injection cylinder is to change the size and the length of the injection nozzle 56. The injection cylinder 57 and nozzle 56 temperature is much higher than the mold temperature. When the nozzle 56 locks into mold injection channel opening, high temperature is needed to ensure the proper flow of Gutta Percha material. Sudden cool off can "freeze" the Gutta Percha material inside the nozzle. A heating element 55 is provided inside the mold around the tip of the nozzle 56 to keep the region around the nozzle opening reasonably warm. The nozzle length and internal diameter are also reduced to reduce Gutta Percha material traveling time from injection cylinder 57 to mold cavity 32. The nozzle's outer diameter is increased so it retains more heat.

Injecting Gutta Percha material requires much higher pressure than injecting plastic. An instant compressed gas chamber system is created to assist hydraulic system to deliver maximum and "instant" pressure needed. A liquid nitrogen gas cylinder is provided to help increase pressure build up speed. Air pressure travels faster than hydraulic pressure. The air pressure system is added at the front of the hydraulic pressure system. When it is ready to inject and pressure system is activated, both air and hydraulic system delivers pressure to give the instant push. This is an important element of obtaining optimum injection time and pressure. Short injection time is preferred, without the negative effect of higher injection pressure. A balance of fast injection (reaction) time and optimum injection pressure is preferred.

Concerning timing of the injection, bigger hydraulic pump with faster reaction time is employed. Since only a very small amount of Gutta Percha material is injected into mold cavities each cycle of injection, and injection time is just a few mile-second, machine needs to build up optimum pressure before injection cylinder screw push out the Gutta Percha material. Further, pressure needs to be activated without delay when screw starts pushing forward, similar to a plunder in a syringe. Computer controlled faster reacting pump further improves injection reaction timing, in addition to gas assisted hydraulic system noted above.

To further secure fast injection time and optimum injection pressure combination, a vacuum line is provided at space just in front of injection nozzle 57, near the main mold channel 47. Before injection starts, vacuum pump will remove most of the air from mold main channel 47 and secondary channels 46. The vacuum pump turned off for injection to take place. This will reduce resistance and increase injection speed. This vacuum feature is preferably used when using a harder type dental Gutta Percha material.

Figure 13:
FIG. 13 is a photograph image of a horizontal injection molding system, in accordance with one embodiment of the present invention.

FIG. 13 is a photograph of a horizontal injection molding system incorporating the features discussed above.

The mold separation process can be further improved by using a mold injection machine having a vertical axis of movement for the mold halve. With this vertical configuration, the stationary (fixed) mold halve 40 is at the bottom, with the moveable mold halve 42 movable with respect to the fixed mold halve 40. This stationary fixed mold halve 40 has the locking stub openings 52 behind the cone cavity chamber to retain the Gutta Percha cones in this mold halve as discussed above, when the top mold halve 42 is lifted and separated. After separation, push rods 54 and 61 from underneath the bottom mold halve 40 (see FIG. 7C) will push the entire molded piece (a rack of cones 10) upward. Then a mechanical robotic arm can be provided to pick up the Gutta Percha cone rack and place it on a conveyer for further processing and packaging.

To further improve production efficiency and throughput, two similar stationary mold halves 40 can be provided side by side, and can move horizontally along precision guide rails or on a precision sliding table, to be place sequentially below the top mold halve 42. The two mold halves 40 therefore take turns to mate with top mold halve 42, so one mold halve 40 would be going through an injection molding cycle while the other mold halve 40 is processed to remove the molded rack of cones and prepared for the next injection cycle.

While the present invention has been described above in connection with the illustrated embodiments, the scope of patent invention covers all possible present and future variations and improvements that is apparent from the disclosure above. While the invention has been particularly shown and described with reference to the preferred embodiments, it will be understood by those skilled in the art that various changes in form and detail may be made without departing from the spirit, scope, and teaching of the invention. Accordingly, the disclosed invention is to be considered merely as illustrative and limited in scope only as specified in the appended claims.

We claim:

1. A method of making a plurality of cones for dental root canal fillings, the method comprising:
   providing a split mold having a plurality of cavities defined in the mold, each corresponding to the shape of a cone; having cooling channels provided in a supporting mold frame to facilitate cooling of the mold after injection, having venting channels at a tip end of the plurality of cavities to vent air to reduce air resistance; having a spray opening in the mold to spray separation lubricating agent into the plurality of cavities to help keep the cavities clean and surface tension low; and having an injection space connected to each of the plurality of cavities;
   providing a split mold injection system, the split mold injection system comprising an injection cylinder, wherein the injection cylinder comprises a small diameter extrusion screw and a plurality of different heating zones;
   injecting Gutta Percha material into the plurality of cavities of the mold using the split mold injection system, wherein the plurality of different heating zones gradually increase the temperature of the Gutta Percha material to the Gutta Percha material's melting point and the small diameter extrusion screw injects the melted Gutta Percha material into the plurality of cavities via the injection space; and
   cooling the mold to set the injected Gutta Percha material, wherein the injected material in the plurality of cavities forms cones after the cooling of the mold, each cone having a body with a tip end, wherein the injected material in the injection space forms a spine after the cooling of the mold, and wherein the cones are connected to the spine when the cones are removed from the mold.

2. The method of claim 1, wherein the split mold comprises a first mold halve and a second mold halve, each defining a plurality of chambers, each chamber having surface features corresponding to one half of a cone to be molded, so that when the first and second mold halves are mated together, the surface features of corresponding chambers in the first and second mold halve together form a corresponding one of the plurality of cavities.

3. The method of claim 2, wherein the first mold halve is provided with a protrusion and/or indent, and the second mold halve is provided with a matching indent and/or protrusion, so that when the first and second mold halves are mated together, the protrusions are received in the indent to provide alignment of the first and second mold halves.

4. The method of claim 3, wherein the protrusion and indent have matching bevel surfaces.

5. The method of claim 4, wherein the injection cylinder injects the Gutta Percha material into the mold under heat and pressure.

6. The method of claim 1, wherein the plurality of cavities in the mold have the same shape, dimension and taper.

7. The method of claim 1, wherein the mold is further configured with an opening leading into the injection space, wherein the step of injecting the material comprises positioning an injector nozzle against the opening to inject the material into the mold, and wherein the method further comprises heating the injector nozzle to maintain flow of the material for injection into the mold.

8. The method of claim 7, wherein the mold is further configured with a heating element disposed around the opening, and wherein the step of heating the injector nozzle uses the heating element to heat a region close to the opening, thereby heating the injector nozzle when it is positioned against the opening.

9. The method of claim 1, wherein the method is for mass producing the plurality of dental root canal filling cones.

10. The method of claim 9, wherein the plurality of cavities in the mold have the same shape, dimension and taper.

11. The method of claim 10, wherein each of the pluralities of the cavities is not shaped without reliance on determining shape of root canal cavity of a dental patient.

12. The method of claim 1, wherein the mold comprises a metal body defining the plurality of cavities.

13. The method of claim 1, wherein the plurality of cavities in the mold comprise a larger open end at one surface and a smaller open end at an opposite surface of the mold;
   wherein the larger end of the plurality of cavity comprises a first taper section and a second taper section;
   wherein the first taper section has a length that extends from smaller open end of the plurality of cavities and provides a space for absorbing back flow pressure when injecting material into the plurality of cavities in the mold; and
   wherein the second taper section has a length that extends from the end of the first taper section and terminates at the surface of the mold.

14. The method of claim 1, wherein the diameter of the tip end ranges between 0.01 to 0.3 mm.

15. The method of claim 1, wherein the diameter of the tip end is less than 1 mm.

16. A method of making a plurality of cones for dental root canal fillings, the method comprising:

providing a split mold having a plurality of cavities defined in the mold, each corresponding to the shape of a cone; wherein the split mold further includes at least one internal channel configured for circulating hot and/or cold water to control the temperature of the mold and an injection space connected to each of the plurality of cavities;

circulating hot water within the at least one internal channel to preheat the mold;

providing a split mold injection system comprising an injection cylinder made from a high strength material and a shortened injection nozzle, wherein the injection cylinder includes a small diameter extrusion screw and a plurality of different heating zones;

injecting Gutta Percha material into the plurality of cavities of the mold using the split mold injection system, wherein the plurality of different heating zones gradually increase the temperature of the Gutta Percha material to the Gutta Percha material's melting point and the small diameter extrusion screw injects the melted Gutta Percha material into the plurality of cavities via the shortened injection nozzle and the injection space; and circulating cold water within the at least one internal channel to cool the mold and to harden the injected Gutta Percha material, wherein the hardened material in the plurality of cavities forms Gutta Percha cones, each cone having a body with a tip end, wherein the hardened material in the injection space forms a spine, and wherein the cones are connected to the spine.

17. The method of claim 16, wherein the diameter of the tip end ranges between 0.01 to 0.3 mm.

18. The method of claim 16, wherein the diameter of the tip end is less than 1 mm.

* * * * *